(12) United States Patent
Fenton et al.

(10) Patent No.: US 7,410,960 B2
(45) Date of Patent: Aug. 12, 2008

(54) METAL COMPLEXES AND THERAPEUTIC USES THEREOF

(75) Inventors: Ronald Ralph Fenton, Padstow Heights (AU); Janice Aldrich-Wright, St. Clair (AU)

(73) Assignees: The University of Western Sydney, Warrington (AU); The University of Sydney, Lidcombe (AU)

( * ) Notice: Subject to any disclaimer, the term of this patent is extended or adjusted under 35 U.S.C. 154(b) by 167 days.

(21) Appl. No.: 10/468,935

(22) PCT Filed: Feb. 22, 2002

(86) PCT No.: PCT/AU02/00167

§ 371 (c)(1),
(2), (4) Date: Mar. 25, 2004

(87) PCT Pub. No.: WO02/066435

PCT Pub. Date: Aug. 29, 2002

(65) Prior Publication Data

US 2004/0152686 A1    Aug. 5, 2004

(30) Foreign Application Priority Data

Feb. 23, 2001  (AU) .................................... PR3302

(51) Int. Cl.
*A01N 55/02*    (2006.01)
*A61K 31/555*    (2006.01)
*C07F 15/00*    (2006.01)

(52) U.S. Cl. ......................................... 514/185; 546/10

(58) Field of Classification Search ................. 514/185; 546/10
See application file for complete search history.

(56) References Cited

U.S. PATENT DOCUMENTS 4,269,834 A * 5/1981 Nauta .......................... 514/187

FOREIGN PATENT DOCUMENTS

| EP | 0 434 444 | 6/1991 |
| EP | 0 434 445 | 6/1991 |
| EP | 0 567 438 | 10/1993 |
| JP | 02032086 | 1/1990 |

OTHER PUBLICATIONS

Entry for "Amine," pp. 29-30 from the McGraw-Hill Concise Encyclopedia of Chemistry © 2004 by the McGraw-Hill Companies, Inc.*

* cited by examiner

*Primary Examiner*—Zachary C Tucker
(74) *Attorney, Agent, or Firm*—Carol L. Francis; Bozicevic, Field & Francis, LLP

(57) ABSTRACT

A compound of formula I or a salt thereof $[ML_1L_2]^{2+}$    (I)

where M is selected from the group consisting of platinum (II), palladium (II) and copper(II); $L_1$ is an intercalator moiety; and $L_2$ is a bidentate ligand, provided that when $L_2$ is other than a bidentate ligand containing an aryl or phenyl group, $L_2$ is a chiral bidentate ligand.

39 Claims, No Drawings

METAL COMPLEXES AND THERAPEUTIC USES THEREOF

CROSS-REFERENCE TO RELATED APPLICATION

This application was filed under 35 U.S.C. §371, and is the U.S. national Stage of PCT/AU02/00167, filed 22 Feb. 2002.

FIELD OF THE INVENTION

The present invention relates to metal complexes and therapeutic uses thereof. The invention is particularly concerned with metallointercalator compounds, pharmaceutical compositions containing them and to their use for the therapeutic treatment of various cancers.

BACKGROUND

The platinum coordination complex cisplatin (cis-diamminedichloroplatinum (II)) is widely prescribed for the treatment of a variety of tumours (eg advanced testicular cancer, ovarian cancer, breast cancer and cancers of the bladder, head, neck, oesophagus and lung). Carboplatin (cis-diammine(1,1-cyclobutanedicarboxylato)platinum (II)) has similar antineoplastic activity and may also be used in bone marrow therapy or peripheral stem cell rescue. U.S. Pat. No. 4,177,263, the entire disclosure of which is incorporated herein by reference, describes methods of treating cancer with cisplatin and cisplatin analogues.

Cisplatin is classified as an alkylating agent. It is believed to kill cancer cells by covalently binding to DNA and interfering with its repair mechanism, eventually leading to cell death. After the cisplatin molecule enters the cell membrane, the first step is for a molecule of water to replace one of the chloride ions of the cisplatin molecule. The resulting complex can then bind to a nitrogen on a DNA nucleotide. The second chloride ion is then replaced by another water molecule and the platinum binds to a second nucleotide. Cisplatin has a preference for nitrogen 7 on two adjacent guanines on the same strand. It also binds to adenine and to a lesser extent across strands. The resulting distortion in shape of the DNA prevents effective repair.

Another covalent binder, oxaliplatin ([Pt(I)xalato (1R), (2R)-diaminocyclohexane] complex) is prescribed for treating the same type of cancers, more particularly cancers of the ovaries, as well as cancers of the colon, of the upper respiratory tracts and epidermoid cancers. Oxaliplatin belongs to the class of platinum(II)-trans-1,2-diaminocyclohexane complexes.

SUMMARY OF INVENTION

We have identified what we believe to be a new group of compounds that may have utility as therapeutic agents in the treatment of cancers.

Accordingly, in a first aspect, the present invention provides a compound of formula I or a salt thereof $$[ML_1L_2]^{2+} \qquad I$$

where M is selected from the group consisting of platinum (II), palladium (II) and copper(II);
$L_1$ is an intercalator moiety; and
$L_2$ is a bidentate ligand,
provided that when $L_2$ is other than a bidentate ligand containing an aryl or phenyl group, $L_2$ is a chiral bidentate ligand.

By the term "intercalator moiety" we mean any moiety that is capable of non-covalent insertion between pairs of bases in the nucleic acid double helix.

Preferably M is platinum(II).

Preferably $L_2$ is a chiral bidentate ligand.

The intercalator moiety preferably forms a square-planar or pseudo-planar complex. The intercalator moiety may be a planar heterocyclic residue. Preferably, the intercalator is a bidentate ligand. A strongly binding bidentate intercalator is particularly preferred.

The intercalator $L_1$ may be 1,10-phenanthroline or a substituted derivative thereof. The 1,10-phenanthroline may be substituted with one or more alkyl groups, preferably methyl groups. Examples of, but not restricted to, substituted derivatives of 1,10-phenanthroline include 4-methyl-1,10-phenanthroline, 5,6-dimethyl-1,10-phenanthroline, 4,7-dimethyl-1,10-phenanthroline, 3,8-dimethyl-1,10-phenanthroline, 3,4,7,8-tetramethyl-1,10-phenanthroline and 4,7-diamino-1,10-phenanthroline.

The substituent positions for 1,10-phenanthroline are shown below:

Substituent positions for 1,10-phenanthroline

The present invention also extends to compounds in which the intercalator compound $L_1$ is other than 1,10-phenanthroline, for example, 2-(2'-pyridyl)quinoxaline, dipyrido[3,2-d; 2'3'-f]quinoxaline (also know as 1,10tetra-aza-2,3-dihydrotriphenylene), diaminophenathrene and their substituted analogues. Whilst compounds based on these other intercalator compounds may be less active as antitumour agents than those based on 1,10-phenanthroline, our experiments in cancer cell lines suggest that they do have antitumour activity.

By the term "chiral bidentate ligand" we mean a bidentate ligand having at least one chiral centre.

Preferably the bidentate ligand is a chiral diamine. Where the diamine is other than a ligand having an aryl or phenyl moiety, the diamine is a chiral diamine. On the other hand, if the diamine contains an aryl or phenyl moiety (eg 1,2-diaminobenzene and substituted analogues thereof), the diamine need not be a chiral diamine. The diamine may be of formula IIa or IIb and variants thereof.

$$R^1R^2N-CHR^3-(C_nH_{2n})-CHR^4-NR^5R^6 \qquad IIa$$

IIb wherein in Formula IIa, the group $-(C_nH_{2n})-$ may be acyclic or cyclic, n is 0 to 4 inclusive, $R^1$, $R^2$, $R^3$, $R^4$, $R^5$ and $R^6$, which may be the same or different, are independently selected from hydrogen or substituted or unsubstituted alkyl, aryl; phenyl or cycloalkyl; or $R^1$, $R^2$, $R^5$ and $R^6$ are as described above and $R^3$ and $R^4$ are joined to form, with the —(C$_n$H$_{2n}$)— group, a cycloalkane having 6 to 8 ring carbons, and wherein the compound of formula IIa has at least one chiral centre, and wherein in Formula IIb, A is an aromatic ring of 6 to 8 carbons, R$^1$, R$^2$, R$^4$ and R$^5$, are as described above; and wherein the compound of formula IIb may or may not have a chiral centre.

An example of a compound of formula IIb that does not require a chiral centre is 1,2-diaminobenzene and derivatives thereof.

In a particularly preferred form of the invention, the compound of formula I is a metal complex exemplified by formula III:

$$[PtL_1L_2]^{2+} \quad\quad\quad III$$

where L$_1$ and L$_2$ are as defined above.

Where the compound of the present invention is in the form of a salt, the anionic counter ion may be any suitable anion. The counter ion may be chosen such that it imparts desirable or special properties, such as increased solubility, on the complex. Preferably the counter ion is pharmaceutically acceptable. Non-limiting examples of anionic counter ions are chloride, perchlorate, hexafluorophosphate, sulfate and nitrate. Chloride ion is the preferred counter ion for biological purposes.

Where compounds of the present invention have a chiral centre, they may be in the form of a substantially pure enantiomer, diasteriomer or a racemate.

We have produced compounds in accordance with formula I and found these compounds to have high biological activity with cancer cell lines. These results are indicative of the compounds of the present invention having biological activity as antitumour agents.

Accordingly, in a second aspect, the present invention provides a method of treatment of a cancer in a subject, comprising administering to the subject a therapeutically effective amount of a compound of formula I or salt thereof $$[ML_1L_2]^{2+} \quad\quad\quad I$$

where M, L$_1$, and L$_2$ are as defined above.

Preferably the compound used in the method of the second aspect is a compound of formula III described above.

The method of treatment of the second aspect may be suitable for treatment of the same range of tumours against which cisplatin, carboplatin and oxaliplatin have been described as being active. Moreover, the compounds of the present invention may be used to treat tumours which have an acquired or intrinsic resistance to cisplatin.

Examples of tumours for which the treatment method of the invention may be used include cancers of the esophagus, breast, ovary; lung (eg small cell carcinoma), bladder, testicles, endometrium, head and neck, thyroid, cervix, neoblastoma, leukemia, and osteogenic sarcoma. The method of the invention may also have application in the treatment of neoplasms of childhood.

The compound unit dose may vary depending upon the host treated, the particular route of administration, and the severity of the illness being treated. Accordingly the optimum dosage may be determined by the practitioner who is treating any particular patient. The antitumour agent of the invention may be administered to a warm-blooded animal at a unit dose of approximately 1-200 mg/kg. The daily dose may be in the range of approximately 40-50 mg/kg, however, as already indicated, the appropriate dosage may be readily determined by the practitioner.

The antitumour effect of the compounds of the present invention may be applied as a sole therapy or may involve, in addition, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer such as a combination of surgery, radiotherapy and/or chemotherapy. In particular, it is known that irradiation or treatment with antiangiogenic and/or vascular permeability reducing agents can enhance the amount of hypoxic tissue within a tumour. Therefore the effectiveness of the compounds of the present invention is expected to be improved by conjoint treatment with radiotherapy and/or with an antiangiogenic agent.

The method of the invention may be used with another anti-cancer agent, for example, adriamycin, radiation, surgery, ultrasound, photoreactive compounds, anthracyclines, nitrogen mustards, ethyleneamines, methylmelamines, alkylsulfonates, nitrosoureas, triazenes, folic acid analogs, pyrimidine analogs, purine analogs and related inhibitors, vinca alkaloids, epipodophyllotoxins, antibiotics, tumour-associated proteins and antigens, biological response modifiers, alpha-interferon, platinum coordination complexes, anthracenedione, substituted ureas, methylhydrazine derivatives, adrenocortical suppressants, adreno-corticosteroid steroids, progestins, estrogens, anti-estrogens, androgens, anti-androgens, and solvents that destroy cancer cells. Further examples of cytotoxic agents that may be used in conjunction with the compound of the invention are paclitaxel, docetaxel, 7-O-methylthiomethyl-paclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4methylcarbonatepaclitaxel, epothilone A, epothilone B, epothilone C, epothilone D, desoxyepothilone A, desoxyepothilone B, S[1S[1R,3R(E), 7R, 10S, 11R, 12R, 16S]]-7,11-dihydroxy-8,8,10,12,16-pentamethyl-3-[1-methyl-2(2-methyl-4-thiazolyl)-ethenyl]-4-aza-17-oxabicyclo [14,1,0]heptadecane-5,9-dione,[1S-[1R,3R(E),7R,10S, 11R, 12R, 16S,]]-3-[2-[2-(aminomethyl)-4-thiazolyl]-1-methyl-ethenyl]-7,11-dihydroxy-8,8,10,12,16-pentamethyl-4,17-dioxabicyclo-[14,1,0]heptadecane-5,9-dione, carminomycin, daunorubicin, aminopterin, methotrexate, methopterin, dichloro-methotrexate, mitomycin C, porfiromycin, 5-fluorouracil, 6-mercaptopurine, gemcitabine, cytosine, arabinoside, podophyllotoxin, etoposide, etoposide phosphate, teniposide, melphalan, vinblastine, vincristine, leurosidine, vindesine, leurosine, estramustine, cyclophosphamide, bleomycin, ifosamide, melphalan, hexamethylmelamine, thiotepa, cytarabin, idatrexate, trimetrexate, dacarbazine, L-asparaginase, camptothecin, CPT11, topotecan, ara-C, bicalutamide, flutamide, leuprolide, a pyridobenzoindole, an interferon and/or an interleukin.

Particular, although not restricted to, examples of combination therapy include the use of a compound in accordance with the present invention with cisplatin, bleomycin, etoposide, vinblastine in the treatment of testicular cancer. In the case of treatment of carcinoma of the ovary, the compound of the invention may be used with, for example, paclitaxel, cyclophosphamide or doxorubicin.

In a third aspect, the present invention provides a pharmaceutical composition comprising a compound in accordance with formula I in an amount sufficient to have an antitumour effect in an animal or human together with at least one pharmaceutically acceptable excipient, diluent and/or carrier.

The compounds of the present invention may be administered in unit dosage form.

The pharmaceutical composition of the invention may be formulated in any suitable form of administration, for example, oral, parenteral (eg intravenous, subcutaneous, intramuscular or intramedullary injection) or rectal administration. Preferably, the composition is formulated for parenteral administration.

The compounds may be administered in conjunction with hydration therapy. This is the "standard" administration method for cisplatin. The hydration therapy minimises/reduces the effect on the kidneys, nephrotoxicity, which is the principal dose limiting factor for treatment.

For oral administration, the pharmaceutical compositions may be in the form of tablets, gelatine capsules, powders, granules or any other form which may be administered orally.

The oral formulation may include components selected from one or more of excipients, carriers, diluents, binders, lubricants; fluidising agents and adhesion inhibitors. The pharmaceutical compositions may further contain pharmaceutically acceptable vehicles that are compatible with the compounds of the invention. In the case of capsules, a conventional excipient such as starch, lactose, talc, magnesium stearate and so on can be used. Also, in the case of tablet, any conventional excipient can be used. Examples of suitable carriers are starch, crystal cellulose, hydroxypropylmethylcellulose, polyethyleneglycol, lactose, polyvinylpyrrolydone or glyceryl or combinations of two or more thereof. Examples of diluents are glucose, dried lactose, Fast-flolactose, dehydrated lactose, sucrose, starch, starch 1500, calcium hydrogen phosphate, emcompress or avicel. Examples of binders are gum arabic, tragacanth, gelatin solution, starch paste solution, glucose syrup, sucrose syrup, povidone or cellulose derivatives. Examples of lubricants include polyethyleneglycol 4000, 6000, 8000, lauryl sodium sulfate, lauryl magnesium sulfate, sodium benzoate, polyethylene monostearate, glyceryl triacetate, magnesium stearate, zinc stearate, calcium stearate, stearic acid, talc, hardened vegetable oil, liquid paraffin, paraffin derivatives or wax. The formulation may include a fluidising agent, for example, starch, talc, silicon dioxide, silicate, magnesium carbonate or magnesium oxide. An adhesion inhibitor, for example starch or talc; may be incorporated into the formulation.

The formulation may be formulated for controlled release. Examples of controlled release additives include hydroxypropylmethylcellulose, hydroxypropylcellulose, hydroxyethylcellulose, ethylcellulose, methylcellulose, carboxymethylcellulose, polyacrylic acid, acrylic acid, acrylate derivatives, poly vinylpyrrolydone or polyethyleneglycol.

Injectable formulations may comprise water-soluble solvents such as physiological saline solution, sterilized water, Ringer's solution, an alcohol (eg ethanol benzylalcohol, propyleneglycol and glycerine), higher fatty acid ester. These injectable formulation may include a diluent, for example, phosphate buffer saline (PBS), 0.9% NaCl (saline) and the like. The formulation may include a preservative, for example, sodium benzoate, methylparaben or propylparaben.

Other additives that may be included in an injectable formulation include an isotonication agent, analgesic, a stabilizing agent, suspending agent, buffering agent, emulsifying agent, all of which are well known to those skilled in the art. The compounds of the present invention may have antimicrobial properties. Accordingly, the present invention extends to antimicrobial composition comprising a compound in accordance with the present invention as well as to the use of these compounds as antimicrobial agents.

Moreover, the compounds of the present invention may have application in the treatment of cell proliferation diseases other than cancers (eg psoriasis). Accordingly, in yet another aspect, the present invention provides antiproliferative compositions comprising a compound in accordance with the invention as well as the use of these compounds as antiproliferative agents.

DETAILED DESCRIPTION OF INVENTION

The compounds of the present invention differ in both structure and method of action from cisplatin and carboplatin (and their analogues). In particular, they differ from cisplatin and carboplatin in that they are intercalators, that is, they are thought to intercalate or insert into DNA, changing the shape and/or structure of the DNA, whereas cisplatin and carboplatin are covalent binders. Moreover, in one embodiment, the new compound of the present invention incorporates a chiral diamine.

Intercalator compounds have been described in *Stereochemical Requirements for Intercalation of Platinum Complexes into Double-Stranded DNA,s*, S. J. Lippard, P. J. Bond, K. C. Wu and W. R. Bauer. *Science*, 194, 726 (1974) *Activity of Platinum Intercalating Agents Against Murine Leukemia L1210*, W. D. McFayden, L. P. G. Wakelin, I. A. G. Roos and V. A. Leopold, *J. Med. Chem.* 28, 1131(1985), the entire disclosure of which are incorporated by reference. Both of these publications relate to non-chiral molecules, as the coordinated diamine. In contrast, the compounds of the present invention either involve the use of chiral alkyl bidentate ligands or non-chiral aryl or phenyl bidentate ligands (eg 1,2-diaminobenzenes) that need not have a chiral centre.

Some platinum complexes currently used contain chiral diamines in their structure, Oxaliplatin being one example. However, the compounds of the present invention differ from such compounds in that they have a bidentate intercalator on the other side of the coordination sphere. In preferred compounds of the invention, this bidentate intercalator is a strongly binding intercalator and as such would be expected to remain coordinated to the divalent platinum molecule under biological conditions.

Furthermore, in a preferred form of the present invention, the compounds of formula I have an overall positive charge (ie. are cationic) on the molecule compared to the neutral cisplatin type compounds, which become charged in vivo through loss chloride ion(s).

The compounds of the present invention may have other advantages such as solubility and mode of action, which may prove to be better than that for drugs currently in clinical use. Changes in the diamine result in changes in properties such as solubility, stereochemistry and activity, adding to the flexibility of use in clinical applications.

In order that the present invention may be more readily understood, we provide that following non-limiting embodiments.

Examples of specific molecular structure of intercalator compounds in accordance with the invention are shown below:

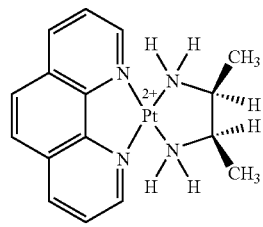

(2S,3R-butanediamine)(1,10-phenanthroline)platinum(II) cation

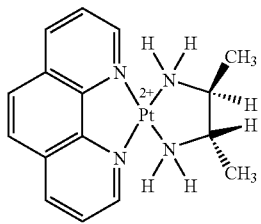

(2S,3S-butanediamine)(1,10-phenanthroline)platinum(II) cation

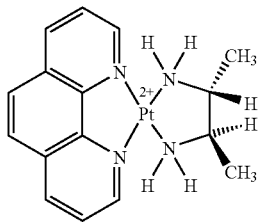

(2R,3R-butanediamine)(1,10-phenanthroline)platinum(II) cation

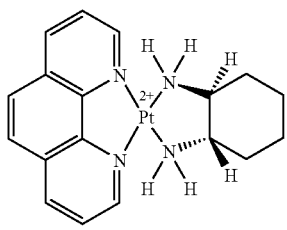

(1S,2S-cyclohexanediamine)(1,10-phenanthroline)platinum(II) cation

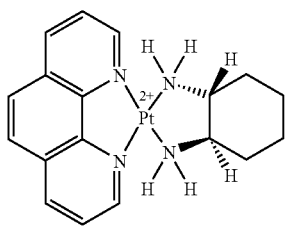

(1R,2R-cyclohexanediamine)(1,10-phenanthroline)platinum(II) cation.

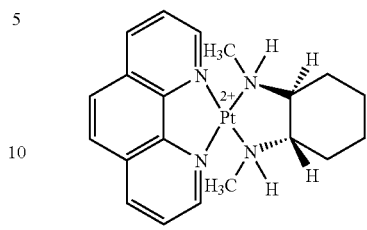

(N,N'-dimethyl-1S,2S-cyclohexanediamine)(1,10-phenanthroline)platinum(II) cation

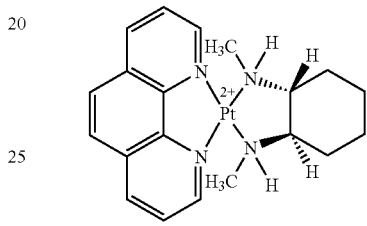

(N,N'-dimethyl-1R,2R-cyclohexanediamine)(1,10-phenanthroline)platinum(II) cation Synthesis of the Platinum(II) Complexes General Synthetic Procedure The following is illustrative of a general synthetic procedure that may be used to make, with appropriate modification, compounds in accordance with the present invention.

Potassium tetrachloroplatinate(II) (0.423 g, 1.02 mmol, Aldrich) was dissolved in 400 mL of water in a large evaporating dish. Sodium chloride (0.529 g, 0.01 mol, Ajax) was added to the solution with gentle stirring until dissolved. The diimine, 1,10-phenanthroline monohydrate (0.202 g, 1.00 mmol, Aldrich), was dissolved in hydrochloric acid (10 M, 0.8 mL) with a minimal amount of water, and added to the initial solution. The reaction was left to slowly evaporate on a steam bath for ~4 hr. The fluffy yellow product was collected via suction filtration and washed with ice-cold water (4×5 mL) and dried in air. The filtrate was preserved and continually reduced by heating, in order to obtain additional crops. The product was collected as described above. Yield: 0.409 g, 90%. The compound was characterized by: $^1$H NMR, solvent DMSO-$d_6$ (Acros Organics), ppm: 8.19 (dd, 2H); 8.29 (s, 2I); 9.06 (d, 2H); 9.79 (d, 2H).

The Synthesis of $[Pt(L)(phen)]^{2+}$ (where L=R,R- or S,S-1, 2-Diaminocyclohexane; N,N'-Dimethyl-R,R- or N,N'-Dimethyl-S,S-1,2-diaminocyclohexane)

The platinum complex, dichloro-1,10-phenanthroline-platinum(II) (~0.50 mmol), was dissolved in water (~100 mL) and gently refluxed with stirring for 1 hr. The diamine, (L), (~0.50 mmol) was dissolved in minimum water and slowly added to the solution via a syringe. The conical flask was covered in aluminium foil and the mixture was left to gently reflux overnight (~16 hr). The next day, a second equivalent of the diamine (L) in minimum water was added to the mixture to ensure completion of the reaction. The solution was gently refluxed for an additional 8 hr. The solution was cooled to room temperature with stirring, and then filtered through a 0.45 μm Sartorius™ Minisart® filter. The solution was reduced to ~50 mL on the rotary evaporator at 40° C.

A saturated solution of lithium perchlorate was added to the ~50 mL solution to precipitate the diamine-platinum complex as a perchlorate salt. The mixture was briefly heated inside the steam bath and then cooled to room temperature. The product was collected via suction filtration using a micro sintered-glass filter. The microcrystalline solid was washed with ice-water (2×5 mL), a minimum volume of ethanol, diethyl ether and dried in air. The product was placed in a vacuum desiccator overnight to dry completely. The filtrate was filtered through a 0.45 μm Sartorius™ Minisart® filter and put aside for crystal formation. The quantities of the reagents used and the yield of each diamine are presented in Table 1.

The [Pt(dach)(phen)]$^{2+}$ complexes were characterized by: $^1$H NMR, solvent DMSOd$_6$ (Acros Organics), ppm: 1.25 (m, 2H); 1.47 (br m, 2H); 1.65 (m, 2H); 2.11 (d, 2H); 2.59 (m, 2H); 6.55 (m, 2H); 7.15 (d, 2H); 8.28 (dd, 2H); 8.37 (s, 2H); 9.15 (m, 2H); 9.20 (s, 2H).

The [Pt(Me$_2$-dach)(phen)]$^{2+}$ complexes were also characterized using: $^1$H NMR, solvent DMSO-d$_6$ (Acros Organics), ppm: 1.25 (m, 2H); 1.50 (m, 1H); 1.70 (m, 4H); 1.95 (m, 1H); 2.90 (d, 3H); 3.05 (d, 3H); 3.15 (br s, 2H); 7.30 (m, 1H); 7.80 (m, 1H); 8.30 (m, 2H); 8.40 (s, 2H); 9.15 (d, 2H); 9.30 (m, 2H).

TABLE 1

The synthetic results of [Pt(L)(phen)](ClO$_4$)$_2$
(where L = R,R- or S,S-1,2-diaminocyclohexane;
N,N'-dimethyl-R,R- or N,N'-dimethyl-
S,S-1,2-diaminocyclohexane)

| Complex | [Pt(R,R-dach)(phen)](ClO$_4$)$_2$ | [Pt(S,S-dach)(phen)](ClO$_4$)$_2$ | [Pt(Me$_2$—R,R-dach)(phen)](ClO$_4$)$_2$ | [Pt(Me$_2$—S,S-dach)(phen)](ClO$_4$)$_2$ |
|---|---|---|---|---|
| [PtCl$_2$(phen)] | 0.223 g, 0.500 mmol | 0.220 g, 0.493 mmol | 0.221 g, 0.500 mmol | 0.224 g, 0.501 mmol |
| (L) 1st equiv. | R,R-dach 0.062 g, 0.540 mmol | S,S-dach 0.061 g, 0.535 mmol | Me$_2$-R,R-dach 0.071 g, 0.571 mmol | Me$_2$-S,S-dach 0.073 g, 0.515 mmol |
| 2nd equiv. | 0.062 g, 0.546 mmol | 0.064 g, 0.559 mmol | 0.071 g, 0.638 mmol | 0.073 g, 0.513 mmol |
| Yield | 0.270 g, 78% | 0.290 g, 85% | 0.260 g, 73% | 0.260 g, 72% |
| Colour | Pale yellow | Pale yellow | Medium yellow | Medium yellow |

IC$_{50}$ Results

The specific cell lines and the IC$_{50}$ results for the various compounds are shown in the Table 2.

TABLE 2

| | Cell lines | | | | |
|---|---|---|---|---|---|
| Compounds | KYSE 520 (esophagus) | A-427 (lung) | LCLC-103H (lung) | 5637 (bladder) | 5637 (bladder) Repeat |
| [Pt(en)(phen)]Cl$_2$ | 49.1 (14.9)* | 24.1 (8.0) | 41.2 (11.6) | 27.0 (3.5) | 23.7 (1.30) |
| [Pt(en)(dpq)]Cl$_2$ | 19.4 (3.1) | 16.4 (6.6) | 23.6 (7.5) | 16.7 (3.1) | |
| [Pt(2R,3R-bn)(phen)]Cl$_2$ | 0.67 (0.03) | 0.54 (0.12) | 0.78 (0.19) | 0.32 (0.18) | 0.43 (0.22) |
| [Pt(2S,3S-bn)(phen)]Cl$_2$ | 1.87 (0.25) | 1.35 (0.84) | 2.39 (0.52) | 1.11 (0.55) | 0.98 (0.38) |
| [Pt(meso-2,3-bn)(phen)]Cl$_2$ | 1.09 (2) | 0.92 (0.13) | 1.07 (0.11) | 0.61 (0.25) | 0.72 (0.25) |
| [Pt(rac-2,3-bn)(phen)]ClO$_4$ | 1.03 (0.33) | 0.67 (0.19) | 1.06 (0.32) | 0.40 (0.14) | 0.95 (0.70) |
| [Pt(pnOH)(phen)]Cl$_2$ | 86.8 (4.9) | 41.7 (12.8) | 97.9 (2) | 66.1 (8.9) | 65.4 (12.47) |
| [Pt(phen)(R,R-dach)](ClO$_4$)$_2$ | | | | | 0.54 (0.44) |
| [Pt(phen)(S,S-dach)](ClO$_4$)$_2$ | | | | | 0.15 (0.06) |
| [Ptphen)(Me$_2$-S,S-dach](ClO$_4$)$_2$ | | | | | 55.6 (13.97) |

TABLE 2-continued

| Compounds | Cell lines | | | | |
|---|---|---|---|---|---|
| | KYSE 520 (esophagus) | A-427 (lung) | LCLC-103H (lung) | 5637 (bladder) | 5637 (bladder) Repeat |
| [Pt(phen)(Me$_2$-R,R-dach)](ClO$_4$)$_2$ | ▨ | ▨ | ▨ | ▨ | 23.6 (8.95) |
| CDDP | 6.63 (1.23) | 4.46 (0.53) | 1.44 (0.45) | 0.88 (0.88) | 0.43 (0.13) |

*The concentrations are in μM (standard deviation)
Shaded areas indicate that no tests have been performed at this stage using these particular cell lines.

When we compare the effect of changing the diamine from the non-chiral 1,2-diaminoethane (en) to the chiral ligands and 2S,3S-diaminobutane (2S,3S-bn) and 2R,3R-diaminobutane (2R,3R-bn) then the concentration inhibiting the exponential growth of cells to 50% is further reduction from 27.0 to 1.11 and 0.32 μM respectively.

On changing the chirality of the diamine such as 2R,3R-diaminocyclohexane (R,R-dach) to 2S,3S-diaminocyclohexane (S,S-dach) then the concentration inhibiting the exponential growth of cells to 50% is even further reduced from 0.54 to 0.15 μM. The IC$_{50}$ value of 2S,3S-diaminocyclohexane (S,S-dach) is lower that cisplatin at 0.43 μM.

From the last two examples it is quite clear that chirality plays a crucial role in the effectiveness of these compounds. Even methylation on the nitrogen atoms (which on coordination to the metal ion produce additional chiral centres) influences the IC$_{50}$ values [Pt(phen)(Me$_2$-S,S-dach)](ClO$_4$)$_2$ and [Pt(phen)(Me$_2$-R,R-dach)](ClO$_4$)$_2$ were 55.6 and 23.6 μM respectively.

These results indicate that a modest variation to either the intercalator or the diamine has significant effects on the resulting IC$_{50}$ values. Systematic variation of each of the components M, L$_1$, L$_3$ in turn to may be used to determine the optimum combination of metal, intercalator and diamine.

Further experiments were carried out and the results of these are shown in Table 3.

TABLE 3

Results Of Anti-Tumor Drug Screening
Unless indicated otherwise, these are the results for growth inhibition studies of compounds using the sulphorhodamine B (SRB) assay. IC$_{50}$ is the concentration required to inhibit cell growth by 50%.

| Compound | Test | Cell line | Results - IC$_{50}$ (μM) |
|---|---|---|---|
| [Pt(Me$_2$—S,S-dach)(phen)](ClO$_4$)$_2$ | CC | L1210 | >40 |
| [Pt(Me$_2$—S,S-dach)(phen)](ClO$_4$)$_2$ | CC | L1210/DDP | >40 |
| [Pt(S,S-dach)(phen)](ClO$_4$)$_2$ | CC | L1210 | 0.13 ± 0.00 |
| [Pt(S,S-dach)(phen)](ClO$_4$)$_2$ | CC | L1210/DDP | 0.28 ± 0.09 |
| [Pt(Me$_2$—R,R-dach)(phen)](ClO$_4$)$_2$ | CC | L1210 | >40 |
| [Pt(Me$_2$—R,R-dach)(phen)](ClO$_4$)$_2$ | CC | L1210/DDP | >40 |
| [Pt(R,R-dach)(phen)](ClO$_4$)$_2$ | CC | L1210 | 1.4, 1.6 |
| [Pt(R,R-dach)(phen)](ClO$_4$)$_2$ | CC | L1210/DDP | 4.3, 4.5 |
| [Pt(Me$_2$—S,S-dach)(phen)](ClO$_4$)$_2$ | CC | L1210 | 12, 12 |
| [Pt(Me$_2$—S,S-dach)(phen)](ClO$_4$)$_2$ | CC | L1210/DDP | 18, 16 |
| [Pt(Me$_2$—R,R-dach)(phen)](ClO$_4$)$_2$ | CC | L1210 | 26, >40 |
| [Pt(Me$_2$—R,R-dach)(phen)](ClO$_4$)$_2$ | CC | L1210/DDP | 34, >40 |
| [Pt(R,R-bn)(phen)]Cl$_2$ | CC | L1210 | 1.5, 1.5 |
| [Pt(R,R-bn)(phen)]Cl$_2$ | CC | L1210/DDP | 2.5, 1.9 |
| [Pt(S,S-bn)(phen)]Cl$_2$ | CC | L1210 | 3.8, 3.0 |
| [Pt(S,S-bn)(phen)]Cl$_2$ | CC | L1210/DDP | 5.3, 8.0 |
| [Pt(S,S-dach)(phen)](ClO$_4$)$_2$ | CC | L1210 | 0.13 ± 0.00 |
| [Pt(S,S-dach)(phen)](ClO$_4$)$_2$ | CC | L1210/DDP | 0.28 ± 0.09 |
| [Pt(R,R-bn)(phen)]Cl$_2$ | SRB | 2008 | 1.7, 4.5 |
| [Pt(R,R-bn)(phen)]Cl$_2$ | SRB | C13 | 5.2, 9.0, 7.4 |
| [Pt(R,R-bn)(phen)]Cl$_2$ | SRB | SKOV3 | 2.0, 4.5, 3.0 |
| [Pt(S,S-bn)(phen)]Cl$_2$ | SRB | 2008 | 7.2, 11 |
| [Pt(S,S-bn)(phen)]Cl$_2$ | SRB | C13 | 26, 22, 28 |
| [Pt(S,S-bn)(phen)]Cl$_2$ | SRB | SKOV-3 | 9.8, 9.2, 12 |
| [Pt(S,S-dach)(phen)](ClO$_4$)$_2$ | SRB | 2008 | 0.37, 0.45 |
| [Pt(S,S-dach)(phen)](ClO$_4$)$_2$ | SRB | C13 | 0.56, 0.88 |
| [Pt(S,S-dach)(phen)](ClO$_4$)$_2$ | SRB | SKOV-3 | 0.31, 0.42 |
| [Pt(R,R-dach)(phen)](ClO$_4$)$_2$ | CC | L1210 | 1.4, 1.6 |
| [Pt(R,R-dach)(phen)](ClO$_4$)$_2$ | CC | L1210/DDP | 4.3, 4.5 |
| [Pt(R,R-dach)(phen)](ClO$_4$)$_2$ | SRB | 2008 | 3.3, 3.1 |
| [Pt(R,R-dach)(phen)](ClO$_4$)$_2$ | SRB | C13 | 5.1, 9.2 |
| [Pt(R,R-dach)(phen)](ClO$_4$)$_2$ | SRB | SKOV3 | 3.3, 3.6 |

Comments:
L1210 cells are mouse leukaemia cells. L1210/DDP are cisplatin-resistant.
Most recent cisplatin controls: L1210 0.5 μM; L1210/DDP 6.9 μM
40 μM is highest dose tested in CC growth inhibition assay
2008 cells are human ovarian carcinoma cells. C13*5 are cisplatin-resistant.
SKOV-3 are intrinsically resistant to cisplatin
Reference IC50's for cisplatin: 2008: 0.6 μM, C13: 10 μM, SKOV-3: 3 μM
Ligands:
dach = 1,2-diaminocyclohexane;
Me$_2$-dach = N,N'-dimethyl-1,2-diaminocyclohexane;
bn = 2,3-butanediamine The data presented in Table3 is the results collected from the growth inhibition studies of selected compounds with the following cell lines: L1210 (mouse leukaemia cells), 2008 (human ovarian carcinoma cells), L1210/DDP and C13*5 (acquired cisplatin resistance) and SKOV-3 (intrinsic cisplatin resistance). The data shows that one of the compounds, [Pt(S,S-dach)(phen)](ClO$_4$)$_2$ has far better activity against all the cell lines tested than the current anti-cancer drug, cisplatin. The data also shows that the bulky cyclohexane ring of the ancillary ligand and the chirality of the substituents on this ring (amine groups) plays an important part in the activity of this particular group of compounds. The complex with the absolute chiralities of S,S exhibits more activity than the R,R enantiomer. Moreover, the data shows that small changes of substitution on the ancillary ligand produces large changes on the activity of the complexes. For example, the complex [Pt(Me2-S,S-dach)(phen)](ClO$_4$)$_2$ (methyl substituent on each of the amine groups) is very much less active than the unsubstituted complex with the same absolute chirality.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any description of prior art documents herein is not an admission that the documents form part of the common general knowledge of the relevant art in Australia.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A compound of formula I or a salt thereof $$[ML_1L_2]^{2+} \qquad \text{I}$$

where M is selected from the group consisting of platinum (II), palladium (II) and copper(II);

L$_1$ is 1,10-phenanthroline or an alkyl-substituted derivative thereof; and L$_2$ is a chiral diamine ligand.

2. A compound according to claim 1, wherein M is platinum(II).

3. A compound according to claim 1, wherein L$_2$ is a compound according to formula IIa or IIb:

$$R^1R^2N\text{—}CH\,R^3\text{—}(C_nH_{2n})\text{—}CHR^4\text{—}NR^5R^6 \qquad \text{IIa}$$

IIb wherein in formula IIa, the group —(C$_n$H$_{2n}$)— may be acyclic or cyclic, n is 0 to 4 inclusive, R$^1$, R$^2$, R$^3$, R$^4$, R$^5$ and R$^6$, which may be the same or different, are independently selected from hydrogen or substituted or unsubstituted alkyl, aryl, or cycloalkyl; wherein the substituted alkyl, aryl, or cycloalkyl is substituted with at least one methyl group, or R$^1$, R$^2$, R$^5$ and R$^6$ are as defined above and R$^3$ and R$^4$ are joined to form, with the —(C$_n$H$_{2n}$)— group, a cycloalkane having 6 to 8 ring carbons, and wherein the compound of formula IIa has at least one chiral centre, and wherein in formula IIb, A is an aromatic ring of 6 to 8 carbons, R$^1$, R$^2$, R$^4$ and R$^5$, which may be the same or different, are independently selected from hydrogen or a substituted or unsubstituted alkyl, aryl, or cycloalkyl, wherein the substituted alkyl, aryl, or cycloalkyl is substituted with at least one methyl group, and wherein the compound of formula IIb includes at least one chiral centre.

4. A compound according to claim 1, wherein the intercalator moiety forms a square-planar or pseudo-planar complex.

5. A compound according to claim 1, wherein L$_1$ is selected from 1,10-phenanthroline or 1,10-phenanthroline substituted with at least one alkyl group.

6. A compound according to claim 5, wherein L$_1$ is selected from the group consisting of 4-methyl-1,10-phenanthroline, 5,6-dimethyl-1,10-phenanthroline, 4,7-dimethyl-1,10-phenanthroline, 3,8-dimethyl-1,10-phenanthroline, 3,4,7,8-tetramethyl-1,10-phenanthroline and 4,7-diamino-1,10-phenanthroline.

7. A compound according to claim 1 which is in the form of a salt.

8. A compound according to claim 7, wherein the counter ion of the salt is selected from the group consisting of chloride, perchlorate, hexafluorophosphate, sulfate and nitrate.

9. A compound according to claim 8, wherein the counter ion is chloride ion.

10. A compound according to claim 1, which is in the form of a racemate.

11. A compound according to claim 1, which is in the form of a diastereomer.

12. A compound according to claim 1, which is in the form of a pure enantiomer.

13. A compound according to claim 1 selected from the group consisting of (2S,3R-butanediamine)(1,10-phenanthroline)platinum(II) cation, (2S,3S-butanediamine)(1,10-phenanthroline)platinum(II) cation, (2R,3R-butanediamine)(1,10-phenanthroline)platinum(II) cation, (1S,2S-cyclohexanediamine)(1,10-phenanthroline)platinum(II) cation, (1R,2R-cyclohexanediamine)(1,10-phenanthroline)platinum(II) cation, (N,N'-dimethyl-1S,2S-cyclohexanediamine)(1,10-phenanthroline)platinum(II) cation and (N,N'-dimethyl-1R,2R-cyclohexanediamine)(1,10-phenanthroline)platinum(II) cation.

14. A method of treatment of a cancer in a subject comprising administering to the subject a therapeutically effective amount of a compound according to claim 1, wherein the cancer is testicular, ovarian, breast, bladder, head and neck, lung, colon, neoblastoma, or epidermoid cancer.

15. A method of treatment of a cancer in a subject comprising administering to the subject a therapeutically effective amount of a compound of formula I or a salt thereof $$[ML_1L_2]^{2+} \qquad \text{I}$$

where M is selected from the group consisting of platinum (II), palladium (II) and copper(II);

L$_1$ is 1,10-phenanthroline or an alkyl-substituted derivative thereof; and

L$_2$ is a chiral diamine ligand, wherein the cancer is testicular, ovarian, breast, bladder, head and neck, lung, colon, neoblastoma, or epidermoid cancer.

16. A method according to claim 15, wherein the compound of formula I is used simultaneously, sequentially or separately with another anticancer therapy selected from surgery, radiotherapy and/or chemotherapy.

17. A method according to claim 16, wherein the compound of formula I is administered with an anticancer compound, a cytotoxic agent and/or a secondary anticancer agent.

18. A method according to claim 17, wherein the compound of formula I is administered with another anticancer compound or cytotoxic agent.

19. A method according to claim 15, wherein M is platinum (II).

20. A method according to claim 15, wherein L$_2$ is a compound according to formula IIa or IIb:

$$R^1R^2N\text{—}CHR^3\text{—}(C_nH_{2n})\text{—}CH\,R^4\text{—}N\,R^5R^6 \qquad \text{IIa}$$

IIb wherein in formula IIa, the group —(C$_n$H$_{2n}$)— may be acyclic or cyclic, n is 0 to 4 inclusive, R$^1$, R$^2$, R$^3$, R$^4$, R$^5$ and R$^6$, which may be the same or different, are independently selected from hydrogen or substituted or unsubstituted alkyl, aryl, or cycloalkyl; wherein the substituted alkyl, aryl, or cycloalkyl is substituted with at least one methyl group, or $R^1$, $R^2$, $R^5$ and $R^6$ are as defined above and $R^3$ and $R^4$ are joined to form, with the —($C_nH_{2n}$)—group, a cycloalkane having 6 to 8 ring carbons, and wherein the compound of formula IIa has at least one chiral centre, and wherein in formula IIb, A is an aromatic ring of 6 to 8 carbons, $R^1$, $R^2$, $R^4$ and $R^5$, which may be the same or different, are independently selected from hydrogen or a substituted or unsubstituted alkyl, aryl, or cycloalkyl, wherein the substituted alkyl, aryl, or cycloalkyl is substituted with at least one methyl group, and wherein the compound of formula IIb includes at least one chiral centre.

21. A method according to claim 15, wherein the intercalator moiety forms a square-planar or pseudo-planar complex.

22. A method according to claim 15, wherein $L_1$ is selected from 1,10-phenanthroline or 1,10-phenanthroline substituted with at least one alkyl group.

23. A method according to claim 22, wherein $L_1$ is selected from the group consisting of 4-methyl-1,10-phenanthroline, 5,6-dimethyl-1,10-phenanthroline, 4,7-dimethyl-1,10-phenanthroline, 3,8-dimethyl-1,10-phenanthroline, 3,4,7,8-tetramethyl-1,10-phenanthroline and 4,7-diamino-1,10-phenanthroline.

24. A method according to claim 15, wherein the compound is in the form of a salt.

25. A method according to claim 24, wherein the counter ion of the salt is selected from the group consisting of chloride, perchlorate, hexafluorophosphate, sulfate and nitrate.

26. A method according to claim 25, wherein the counter ion is chloride ion.

27. A method according to claim 15, which is in the form of a racemate.

28. A method according to claim 15, which is in the form of a diastereomer.

29. A method according to claim 15, which is in the form of a pure enantiomer.

30. A method according to claim 15, wherein the compound is selected from the group consisting of (2S,3R-butanediamine)(1,10-phenanthroline)platinum(II) cation, (2S,3S-butanediamine)(1,10-phenanthroline)platinum(II) cation , (2R,3R-butanediamine)(1,10-phenanthroline)platinum(II) cation, (1S,2S-cyclohexanediamine)(1,10-phenanthroline)platinum(II) cation, (1R,2R-cyclohexanediamine)(1,10-phenanthroline)platinum(II) cation, (N,N'-dimethyl-1S,2S-cyclohexanediamine)(1,10-phenanthroline)platinum(II) cation and (N,N'-dimethyl-1R,2R-cyclohexanediamine)(1,10-phenanthroline)platinum(II) cation.

31. A method according to claim 15, wherein M is palladium(II).

32. A method according to claim 15, wherein M is copper (II).

33. A pharmaceutical composition comprising a compound in accordance with formula I $$[ML_1L_2]^{2+} \qquad \qquad I$$

where M is selected from the group consisting of platinum (II), palladium (II) and copper(II);

$L_1$ is 1,10-phenanthroline or an alkyl-substituted derivative thereof; and $L_2$ is a chiral diamine ligand, in an amount sufficient to have an antitumour effect in an animal or human together with at least one pharmaceutically acceptable excipient, diluent and/or carrier.

34. A pharmaceutical composition according to claim 33 in a form suitable for oral, parenteral or rectal administration.

35. A composition according to claim 34 in an injectable form.

36. A composition according to claim 34 in a dosage form selected from the group consisting of tablets, capsules and powders.

37. A composition according to claim 33, wherein the compound of formula I is (2S,3R-butanediamine)(1,10-phenanthroline)platinum(II) cation, (2S,3S-butanediamine)(1,10-phenanthroline)platinum(II) cation , (2R,3R-butanediamine)(1,10-phenanthroline)platinum(II) cation, (1S,2S-cyclohexanediamine)(1,10-phenanthroline)platinum(II) cation, (1R,2R-cyclohexanediamine)(1,10-phenanthroline) platinum(II) cation, (N,N'-dimethyl-1S,2S-cyclohexanediamine)(1,10-phenanthroline)platinum(II) cation and (N,N'-dimethyl-1R,2R-cyclohexanediamine)(1,10-phenanthroline)platinum(II) cation.

38. A compound according to claim 1, wherein M is palladium(II).

39. A compound according to claim 1, wherein M is copper (II).

* * * * *

UNITED STATES PATENT AND TRADEMARK OFFICE
CERTIFICATE OF CORRECTION

PATENT NO. : 7,410,960 B2 Page 1 of 1
APPLICATION NO. : 10/468935
DATED : August 12, 2008
INVENTOR(S) : Ronald Ralph Fenton It is certified that error appears in the above-identified patent and that said Letters Patent is hereby corrected as shown below:

Claim 4 on col. 13, lines 54-56 should read:

4. A compound according to claim 1, wherein ~~the intercalator moiety~~ $\underline{L_1}$ forms a square-planar or pseudo-planar complex.

Claim 21 on col. 15, lines 14-16 should read:

21. A compound according to claim 15, wherein ~~the intercalator moiety~~ $\underline{L_1}$ forms a square-planar or pseudo-planar complex.

Signed and Sealed this

Eleventh Day of November, 2008

JON W. DUDAS
*Director of the United States Patent and Trademark Office*